US00PP09064P

United States Patent [19]

Evers

[11] Patent Number: Plant 9,064

[45] Date of Patent: Feb. 28, 1995

[54] HYBRID TEA ROSE PLANT NAMED TANALEPHAR

[75] Inventor: Hans Evers, Uetersen, Germany

[73] Assignee: Bear Creek Gardens, Inc., Medford, Oreg.

[21] Appl. No.: 269,344

[22] Filed: Jun. 29, 1994

[51] Int. Cl.[6] ..... A01H 5/00

[52] U.S. Cl. ..... Plt./12

[58] Field of Search ..... Plt. 11, 12, 16, 19, Plt. 20

*Primary Examiner*—Howard J. Locker

*Attorney, Agent, or Firm*—Klarquist Sparkman Campbell Leigh & Whinston

[57] ABSTRACT

A hybrid tea rose plant having a low petal count; thick, leathery petals; strong, vigorous, upright growth; unusual orange-red flower color, and a very long vase life.

1 Drawing Sheet

The present invention relates to a new and distinct variety of rose plant of the hybrid tea class which was originated by me by crossing an unnamed seedling with the unpatented variety TANettelur.

The primary objective of this breeding was to produce a rose variety having the long stems and orange-red color of the female parent combined with the excellent vase life, large flowers and orange-red flower color of the male parent. The objective was substantially achieved, along with other desirable improvements, as evidenced by the following unique combination of characteristics that are outstanding in the new variety and that distinguish it from its parents, as well as from all other varieties of which I am aware:

1. Unusual orange-red flower color;
2. Exceptionally long vase life;
3. Few petals, but very thick and leathery;
4. Vigorous, upright growth; and
5. Long, straight stems.

Asexual reproduction of this new variety by budding, as performed at Uetersen, Germany, and at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour chart, except where ordinary dictionary significance of color is indicated.

Parentage:

*Seed parent.*—An unnamed seedling.

*Pollen parent.*—TANettelur (not patented in U.S.A.).

Classification:

*Botanical.*—*Rosa hybrida.*

*Commercial.*—Hybrid tea.

FLOWER

Observations made from specimens grown in a greenhouse environment at Uetersen, Germany, and Somis, Calif., from October, 1993, through March 1994.

Blooming habit: Recurrent.

Bud:

*Size.*—2 inches when the petals start to unfurl.

*Form.*—The bud form is long, pointed ovoid.

*Color.*—When sepals first divide, bud color is Red Group 51B with a darker edge to the petals (Red Group 46B). The bases of the petals are White Group 155B. When half blown, the upper sides of the petals are Red Group 43C; and the lower sides of the petals are Red Group 51B, with the bases of the petals White Group 155B.

*Sepals.*—Color: Green Group 143C. Surface texture: Covered in fine hairs. There are three normally to heavily appendaged sepals. There are two unappendaged sepals with hairy edges.

*Receptacle.*—Color: Green Group 143C. Shape: Funnel. Size: Broad ($\frac{1}{2}$ inch wide$\times\frac{3}{8}$ inch long). Surface: Smooth.

*Peduncle.*—Length: Medium ($3\frac{1}{2}$ inches). Surface: Smooth. Color: Light green. Strength: Stiff, erect, heavy.

Bloom:

*Size.*—Large. Average open size is 5 inches.

*Borne.*—Singly.

*Stems.*—Long (average length is about 24 to 28 inches), strong.

*Form.*—When first open: High centered. Permanence: Retains its form to the end, but other edges curl slightly.

*Petalage.*—Number of petals under normal conditions: 20.

*Color.*—The upper side of the petals is Red Group 43C. The reverse side of the petals is Red Group 51B. The base of each petal has a yellow half-moon ($\frac{3}{8}$ inch wide$\times\frac{1}{4}$ inch long) at the point of attachment. The major color on the upper side is Red Group 43C.

*Variegations.*—None.

*Discoloration.*—The general tonality at the end of the first day: No change. At the end of the third day: No change.

*Fragrance.*—Slight.

Petals:

*Texture.*—Thick, leathery.

*Shape.*—Round.

*Form.*—Tips slightly recurved.

*Arrangement.*—Imbricated, with no petaloids in the center.

*Persistence.*—Hang on and dry.

*Lastingness.*—On the plant: Very long (14 days). As a cut flower: Very long (18 days).

Reproductive parts:

*Anthers.*—Size: Medium. Quantity: Many. Color: Greenish white. Arrangement: Regular around styles.

*Filaments.*—Color: Reddish brown.

*Pollen.*—Color: Lemon yellow.

*Styles.*—Color: Red.

*Stigmas.*—Color: Greenish white.

Form: Bush.

Growth: Very vigorous, upright, branching. At one year, the plant is, in a greenhouse in Somis, Calif., 6 feet tall and 3½ feet wide.

Foliage: Number of leaflets on normal mid-stem leaves: 5 or 7.

*Size.*—Very large (6½ inches long × 5 inches wide).

*Quantity.*—Normal.

*Color.*—New foliage: Greyed-Purple Group 187A upper side; Greyed-Purple Group 184A lower side. Old foliage: Green Group 135A upper side; Green Group 138A lower side.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth, with occasional prickles.

*Stipules.*—Short ½ inch), serrated, bearded.

*Disease resistance.*—Susceptible to mildew under normal growing conditions in a greenhouse at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—¼ inch to ⅜ inch long; hooked slightly downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its low petal count; thick, leathery petals; strong, vigorous, upright growth; unusual orange-red flower color, and a very long vase life.

* * * * *

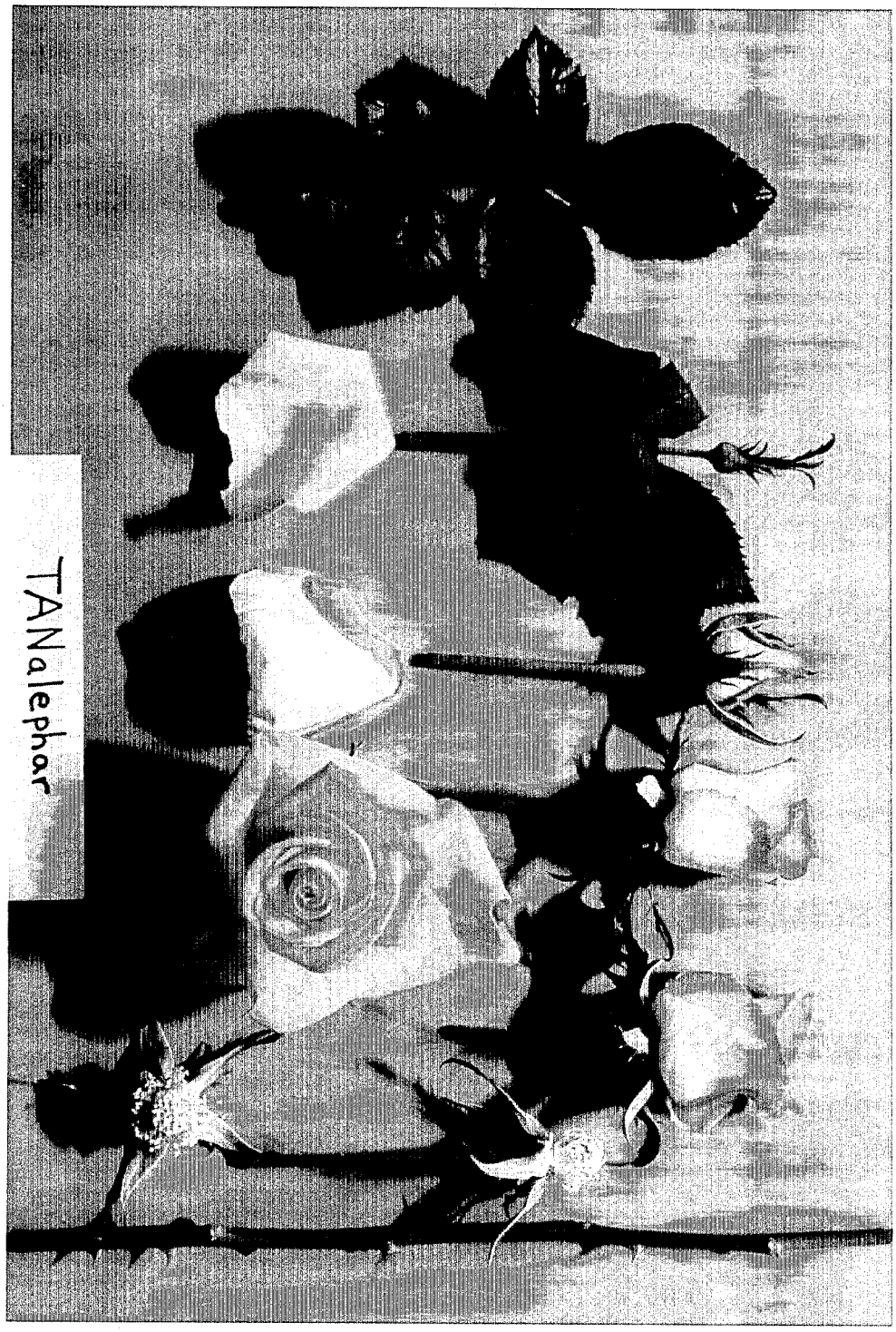
TANalephar